US006515125B1

(12) United States Patent
Slack et al.

(10) Patent No.: US 6,515,125 B1
(45) Date of Patent: Feb. 4, 2003

(54) LIQUID PARTIALLY TRIMERIZED POLYISOCYANATES BASED ON TOLUENE DIISOCYANATE AND DIPHENYLMETHANE DIISOCYANATE

(75) Inventors: William E. Slack, Moundsville, WV (US); Hersel T. Kemp, II, New Martinsville, WV (US); Kenneth P. Yonek, Eighty Four, PA (US)

(73) Assignee: Bayer Corporation, Pittsburgh, PA (US)

( * ) Notice: Subject to any disclaimer, the term of this patent is extended or adjusted under 35 U.S.C. 154(b) by 0 days.

(21) Appl. No.: 09/803,261

(22) Filed: Mar. 9, 2001

(51) Int. Cl.[7] .................. C07D 251/34; C07C 271/28; C07C 271/26; C07C 269/02; C08G 18/79
(52) U.S. Cl. .............. 544/222; 252/182.2; 252/182.21; 252/182.22; 528/67; 528/73; 528/76; 528/77; 544/193; 560/25; 560/26; 560/330; 560/336; 560/359; 560/360
(58) Field of Search .................. 252/182.2, 182.21, 252/182.22; 528/67, 73, 76, 77; 544/193, 222; 560/25, 26, 330, 336, 359, 360

(56) References Cited

U.S. PATENT DOCUMENTS

| 4,255,569 A | 3/1981 | Müller et al. ................ 544/193 |
| 4,284,730 A | 8/1981 | Narayan et al. ............. 521/160 |
| 4,326,043 A | 4/1982 | Narayan et al. ............. 521/137 |
| 4,359,541 A | 11/1982 | Patton, Jr. et al. .......... 521/137 |
| 4,359,550 A | 11/1982 | Narayan et al. ............. 524/871 |
| 4,379,905 A | 4/1983 | Stemmler et al. ............. 528/73 |
| 4,382,125 A | 5/1983 | Narayan et al. ............. 521/160 |
| 4,456,709 A | 6/1984 | Richter et al. ............... 521/160 |
| 4,518,729 A | 5/1985 | Breidenbach et al. ........ 524/101 |
| 4,518,761 A | 5/1985 | Richter et al. ................. 528/67 |
| 4,552,902 A | 11/1985 | Nafziger et al. ............. 521/129 |
| 4,743,627 A | 5/1988 | Narayan et al. ............. 521/160 |
| 4,772,639 A | 9/1988 | Pilger et al. ................. 521/124 |
| 5,102,918 A | 4/1992 | Moriya ........................ 521/110 |
| 5,124,370 A | 6/1992 | Scholl et al. ................ 521/161 |
| 5,204,409 A | 4/1993 | Arend et al. ................. 525/123 |
| 5,319,058 A | 6/1994 | Hattori et al. ................. 528/67 |
| 5,723,564 A | 3/1998 | Schmalstieg et al. ......... 528/73 |
| 5,798,431 A | 8/1998 | Brahm et al. ................. 528/73 |
| 6,028,158 A | 2/2000 | Slack et al. ................... 528/44 |
| 6,063,891 A | 5/2000 | Slack et al. ................... 528/59 |

FOREIGN PATENT DOCUMENTS

| CA | 2113890 | 8/1994 |
| DE | 34 20 923 A1 | 12/1985 |
| GB | 1337659 | 10/1971 |

Primary Examiner—Rabon Sergent
(74) Attorney, Agent, or Firm—Joseph C. Gil; N. Denise Brown

(57) ABSTRACT

This invention relates to storage-stable, liquid, partially trimerized polyisocyanates having an NCO group content of 24 to 40% by weight, and comprising 20 to 88% by weight of toluene diisocyanate and 12 to 80% by weight of a polyisocyanate of the diphenylmethane series. The present invention also relates to a process for the preparation of the storage-stable, liquid, partially trimerized polyisocyanates; to storage-stable, liquid urethane prepolymers of these partially trimerized polyisocyanates; and to a process for the production of these storage-stable, liquid, urethane prepolymers.

22 Claims, No Drawings

LIQUID PARTIALLY TRIMERIZED POLYISOCYANATES BASED ON TOLUENE DIISOCYANATE AND DIPHENYLMETHANE DIISOCYANATE

BACKGROUND OF THE INVENTION

This invention relates to liquid, partially trimerized polyisocyanate compositions. These liquid polyisocyanate products have an NCO group content of from 24 to 40% by weight, and comprise the partial trimerization product of: (A) 20 to 88% by weight of toluene diisocyanate, and (B) 12 to 80% by weight of a polyisocyanate of the diphenylmethane series, with the sum of the %'s by weight of (A) and (B) totalling 100% by weight. This invention also relates to a process for the preparation of these liquid polyisocyanate compositions which contain isocyanurate groups and have an NCO group content of 24 to 40%.

The trimerization of aromatic isocyanates to form polyisocyanurates is well known in the art. U.S. Pat. Nos. 4,743,627 and 4,382,125 both describe the partial trimerization of polymethylene polyphenylene polyisocyanate (p-MDI), having an average functionality of >2.2, to give stable liquid products having relatively high viscosity at 25° C. (i.e., 2000–100,000 mPa.s).

U.S. Pat. No. 4,284,730 relates to the trimerization of monomeric MDI which has been partially converted to carbodiimide/uretonimine, to give stable liquid polyisocyanurate compositions.

U.S. Pat. No. 5,124,370 describes liquid polyisocyanate mixtures containing isocyanurate groups and having an NCO content of 15 to 30% by weight. These mixtures are obtained by partial trimerization of the isocyanate groups of polyisocyanate mixtures of the diphenylmethane series containing 80 to 100% by weight diisocyanate diphenylmethane isomers and 0 to 20% by weight higher ring compounds of the diisocyanate diphenylmethane series.

The trimerization of toluene diisocyanate in a solvent to make a storage stable liquid is described in both U.S. Pat. No. 4,379,905 and DE 19,523,657. These products are disclosed as being suitable as isocyanate components in two-component polyurethane lacquers.

U.S. Pat. No. 4,456,709 describes storage-stable liquid polyisocyanates which have an NCO group content of 36.5 to 45%. These are prepared by mixing 25 to 70 parts of partially trimerized 2,4-TDI with 75 to 30 parts of unmodified 2,4- and/or 2,6-TDI.

Canadian Patent Application 2,113,890 relates to trimer catalyst systems for aliphatic and aromatic isocyanates. The trimer catalyst systems of this earlier application comprise (A) a lithium compound selected from the group consisting of: (i) lithium salts of aliphatic or aromatic monocarboxylic or dicarboxylic acids, (ii) lithium salts of hydroxyl group containing compounds having from 1 to 3 hydroxyl groups per compound, wherein the hydroxyl groups are directly attached to an aromatic ring, and (iii) lithium hydroxide; and (B) an organic compound containing at least one hydroxyl group. These trimer catalyst systems result in partially trimerized isocyanates which additionally can contain a significant amount of urethane groups.

In accordance with the disclosures of U.S. Pat. No. 4,379,905 and DE 19,523,657, it is necessary that a solvent be present in order to form liquid products. Due to the large quantity of solvent present, these products have restricted uses. In particular, these products are clearly designed for use in coatings applications only.

U.S. Pat. No. 4,456,709 requires pure 2,4-toluene diisocyanate in the first step. The process in this reference results in final products having a relatively narrow NCO content and a restricted distribution of oligomers due to the fact that the trimerization must be completed in the first step of the process.

U.S. Pat. Nos. 6,028,158 and 6,063,891 disclose freeze-stable, allophanate-modified toluene diisocyanurates having an NCO group content of about 15 to about 42%. These freeze-stable compositions are prepared by reacting A) toluene diisocyanate, and B) an organic compound containing at least one hydroxyl group, in the presence of a catalytic amount of C) at least one allophanate-trimer catalyst, or an allophanate-trimer catalyst system. These compositions contain both isocyanurate groups and allophanate groups. Also, this patent discloses blends of these allophanate-modified toluene diisocyanurates with polymethylene poly(phenylisocyanates) (i.e. PMDI), wherein the blend has an NCO content of about 16.8 to 41.6%; and urethane prepolymers of these allophanate-modified toluene diisocyanurates, as well as the blends of these with PMDI, which have NCO group contents of from about 14 to about 40%.

U.S. Pat. No. 4,518,761 discloses a process for the preparation of mixed trimers by at least partially trimerizing the isocyanate groups of two isocyanate components with different reactivities (with respect to trimerization) in the presence of a trimerization catalyst, and mixed trimers prepared by this process. The process comprises (a) adding a less reactive isocyanate component to a vessel, (b) trimerizing at least about 0.1% of the isocyanate groups of the less reactive isocyanate component in the presence of a trimerization catalyst, (c) metering the more reactive isocyanate component into the reaction vessel, and optionally, (d) terminating the trimerization reaction at the desired degree of trimerization by thermal decomposition of the trimer catalyst and/or adding a catalyst stopper/poison. It is essential according to the '761 patent, that the two isocyanate components have different reactivities. Thus, it is possible to use an isocyanate having aliphatically bound and/or cycloaliphatically bound isocyanate groups with an isocyanate having aromatically bound isocyanate groups; or to use an isocyanate having aliphatically or cycloaliphatically bound isocyanate groups with an isocyanate having heteroaromatically bound isocyanates groups; etc. Since aliphatic isocyanates give liquid trimer products, this approach allows for the incorporation of an aromatic isocyanate into a trimer product that could be a liquid. It is not, however, disclosed or suggested by U.S. Pat. No. 4,518,761 that two different aromatic isocyanate components can be used to form a liquid product.

Although U.S. Pat. No. 4,772,639 relates to a process for the production of molded polyurethane, it also discloses polyisocyanate mixtures that contain trimer groups. These isocyanates are either (1) mixtures of (i) isophorone diisocyanate and (ii) a polyisocyanate containing isocyanurate groups based on 1,6-diisocyanato-hexane; or (2) mixtures of (i) isophorone diisocyanate and (ii) a polyisocyanate containing isocyanurate groups based on 1,6-diisocyanato-hexane and isophorone diisocyanate.

U.S. Pat. No. 5,798,431 describes a process for the production of polyisocyanates containing isocyanurate groups by catalytically trimerizing a mixture of a) a low molecular weight isocyanate component having aliphatically bound isocyanate groups, an average molecular weight of 128 to 800 and an average NCO functionality of 1.7 to 2.2, and b) a low molecular weight isocyanate component having an aromatically bound isocyanate groups, an average molecular weight of 148 to 800 and an average NCO functionality of 1.7 to 2.2, in the presence of c) an aminosilyl compound. Any excess distillable isocyanate is subsequently removed to form a polyisocyanate having a monomer content of less than 0.7%, based on the weight of polyisocyanate solids. The examples are directed to toluene diisocyanate and hexamethylene diisocyanate.

A process for the preparation of a polyurea resin is disclosed by U.S. Pat. No. 5,319,058. It comprises (A) mixing (a) an aromatic polyamine component which comprises a combination of at least two aromatic polyamine compounds corresponding to specified formulas and (b) an aliphatic polyisocyanate to form a mixture, and (B) heating the mixture to effect the reaction between the amino groups and the isocyanato groups. Suitable polyisocyanates for component (b) comprise (b1) an aliphatic diisocyanate, and (b2) a cyclic trimer of an aliphatic polyisocyanate.

U.S. Pat. No. 5,102,918 describes a process for producing a modified organic polyisocyanate having an isocyanurate ring. This process comprises adding a trimerization catalyst, an organic phosphite ester and a surfactant (and optionally a ferrocene compound) to an organic polyisocyanate and/or a partially urethanized organic polyisocyanate to form isocyanurate groups of not more than 20% of the total of isocyanate groups. A stopper is added, if necessary. Suitable organic polyisocyantes include both TDI and MDI. Example 18 appears to use MDI and TDI.

U.S. Pat. No. 4,255,659 discloses that isocyanates of differing reactivities are suitable for the process described therein (see column 2, lines 16–23). These include mixtures of TDI and IPDI, and appears to be similar to the '761 patent discussed above.

Carbodiimide and/or uretonimine-isocyanurate-containing polyisocyanates are described by U.S. Pat. No. 4,284,730. These can be prepared by (a) partial trimerization of a mixture of a polyisocyanate and a polyisocyanate-uretonimine with trimer catalysts to the desired free isocyanate level, (b) sequential partial carbodiimidization to uretonimine followed by partial trimerzation of a polyisocyanate, (c) sequential trimerization of the polyisocyanate followed by partial carbodiimidization, (d) simultaneous conversion using a mixed catalyst system of carbodiimide and isocyanurate catalysts, (e) blending liquid polyisocyanate with a polyisocyanate-uretonimine mixture and a polyisocyanate-isocyanurate mixture (see column 2, lines 37–50).

U.S. Pat. Nos. 4,326,043, 4,359,541 and 4,359,550 each describes dispersible polyisocyanurate polymers. Suitable isocyanates are disclosed broadly, including mixtures of TDI, MDI and PMDI. This reference also discloses that the isocyanate can be converted to a trimer in a solvent which is a solid, and then dispersed in a polyol. Examples 48–84 of the '043 patent disclose the dispersed trimer solid containing catalysts, surfactants, etc., is reacted with the isocyanate blend of TDI/MDI (80:20) to form a foam.

Stable solutions of trimerized isocyanate prepolymers in monomeric polyisocyanates are described by the U.S. Pat. No. 4,552,902 patent. First an isocyanate-terminated prepolymer is made, then a cotrimer is formed by trimerizing the NCO-terminated prepolymer with MDI or PMDI. The cotrimer is reacted with an excess of a low equivalent weight polyahl to form another isocyanate-terminated prepolymer. TDI is suitable for forming the first NCO-terminated prepolymer. The examples all use TDI and MDI, and various polyols to form the prepolymers. It is expressly stated at column 5, lines 50–55, that the diols must be present for the products to be liquids. Also, the first step of making a prepolymer followed by the addition of the second isocyanate, then trimerizing the mixture will result in allophanate formation.

GB 1,337,659 describes a polyisocyanate solution which comprises a solution of at least one polyisocyanate containing at least one isocyanuric acid ring dissolved in a monomeric polyisocyanate which is free from isocyanurate groups. These are not mixed trimers, but rather are a TDI trimer mixed with a TDI prepolymer. Only Example 5 describes the preparation of a mixed trimer product from MDI and TDI with 1,2-propylene glycol. However, this product contains less than 3% by weight of trimer, and there is no evidence that it would be a stable liquid product. None of the final isocyanate products in these working examples are pure mixed trimers. Rather, each of these products contains some urethane and/or allophanate groups, and contains a relatively small quantity of trimer groups. Allophanate modifications tend to form liquid products. Therefore, these products would be expected to be liquids.

Partial trimerization of TDI always leads to a product that forms solids on storage at 25° C. Partial trimerization of MDI containing >80% by weight of 4,4'-MDI will also always form solids at 25° C. The current invention allows for the preparation of partial trimerization products which are solid-free liquids at 25° C., by the partial trimerization of a specific mixture of TDI and MDI. The products made by the present invention can have a high % by weight of trimer (i.e. 20–65%) without the need to include other modifications such as, for example, urethane, allophanate, or carbodiimide, to prevent solids formation at 25° C.

SUMMARY OF THE INVENTION

This invention relates to storage-stable liquid, partially trimerized polyisocyanate compositions. These storage-stable liquid, partially trimerized polyisocyanates have an NCO group content of 24 to 40% by weight, preferably 26 to 38% by weight, and most preferably of 28 to 36% by weight. The liquid polyisocyanates of the present invention comprise the partial trimerization product of:

(A) from 20 to 88% by weight of toluene diisocyanate having an isomer distribution of:
   (1) from 60 to 100% by weight of the 2,4-isomer, and
   (2) from 0 to 40% by weight of the 2,6-isomer, with the sum of the %'s by weight of (A)(1) and (A)(2) totalling 100% by weight of (A); and (B) from 12 to 80% by weight of a polyisocyanate of the diphenylmethane series comprising from:
   (1) 0 to 50% by weight of higher functionality polyisocyanates of the diphenylmethane series,
   (2) 40 to 100% by weight of 4,4'-diphenylmethane diisocyanate,
   (3) 0 to 20% by weight of 2,4'-diphenylmethane diisocyanate, and
   (4) 0 to 6% by weight of 2,2'-diphenylmethane diisocyanate,
   with the sum of the %'s by weight of (B)(1), (B)(2), (B)(3) and (B)(4) totalling 100% by weight of (B);
wherein the sum of the %'s by weight of (A) and (B) total 100% by weight.

The present invention also relates to a process for the preparation of these storage-stable, liquid polyisocyanate compositions having an NCO group content of 24 to 40%, preferably 26 to 38%, and most preferably 28 to 36%, and which contain isocyanurate groups. This process comprises:

(1) partially trimerizing:
   (A) from 20 to 88% by weight of toluene diisocyanate having an isomer distribution of:
      (1) from 60 to 100% by weight of the 2,4-isomer, and
      (2) from 0 to 40% by weight of the 2,6-isomer, with the sum of the %'s by weight of (A)(1) and (A)(2) totalling 100% by weight of (A); and
   (B) from 12 to 80% by weight of a polyisocyanate of the diphenylmethane series comprising from:
      (1) 0 to 50% by weight of higher functionality polyisocyanates of the diphenylmethane series,
      (2) 40 to 100% by weight of 4,4'-diphenylmethane diisocyanate,
      (3) 0 to 20% by weight of 2,4'-diphenylmethane diisocyanate, and
      (4) 0 to 6% by weight of 2,2'-diphenylmethane diisocyanate,
      with the sum of the %'s by weight of (B)(1), (B)(2), (B)(3) and (B)(4) totalling 100% by weight of (B);
   wherein the sum of the %'s by weight of (A) and (B) total 100% by weight, in the presence of:
      (C) at least one trimerization catalyst, followed by the addition of:
      (D) an acidic stopper.

The present invention also relates to storage-stable, liquid prepolymers containing the mixed trimers described above. More specifically, these storage-stable, liquid prepolymers contain a mixed trimer of toluene diisocyanate and a polyisocyanate of the diphenylmethane series and have an NCO group content of about 10 to about 38%. These prepolymers comprise the reaction product of:

(I) the liquid, partially trimerized polyisocyanates having an NCO group content of 24 to 40% by weight, preferably 26 to 38% by weight, and most preferably of 28 to 36% by weight, and which comprise the partial trimerization product of:
   (A) from 20 to 88% by weight of toluene diisocyanate having an isomer distribution of:
      (1) from 60 to 100% by weight of the 2,4-isomer, and
      (2) from 0 to 40% by weight of the 2,6-isomer, with the sum of the %'s by weight of (A)(1) and (A)(2) totalling 100% by weight of (A); and
   (B) from 12 to 80% by weight of a polyisocyanate of the diphenylmethane series comprising from:
      (1) 0 to 50% by weight of higher functionality polyisocyanates of the diphenylmethane series,
      (2) 40 to 100% by weight of 4,4'-diphenylmethane diisocyanate,
      (3) 0 to 20% by weight of 2,4'-diphenylmethane diisocyanate, and
      (4) 0 to 6% by weight of 2,2'-diphenylmethane diisocyanate, with the sum of the %'s by weight of (B)(1), (B)(2), (B)(3) and (B)(4) totalling 100% by weight of (B);
   wherein the sum of the %'s by weight of (A) and (B) total 100% by weight; and
(II) an organic component containing from about 1.5 to about 4 hydroxyl groups, preferably 1.8 to 3 hydroxyl groups, and having a molecular weight of from about 76 to about 6,000, preferably of about 76 to about 4,800.

The present invention also relates to a process for the production of these storage-stable, liquid prepolymers containing a mixed trimer of toluene diisocyanate and a polyisocyanate of the diphenylmethane series and having an NCO group content of about 10 to about 38%. This process comprises:

(1) reacting
(I) the liquid, partially trimerized polyisocyanates having an NCO group content of 24 to 40% by weight, preferably 26 to 38% by weight, and most preferably of 28 to 36% by weight, and which comprise the partial trimerization product of:
   (A) from 20 to 88% by weight of toluene diisocyanate having an isomer distribution of:
      (1) from 60 to 100% by weight of the 2,4-isomer, and
      (2) from 0 to 40% by weight of the 2,6-isomer, with the sum of the %'s by weight of (A)(1) and (A)(2) totalling 100% by weight of (A); and
   (B) from 12 to 80% by weight of a polyisocyanate of the diphenylmethane series comprising from:
      (1) 0 to 50% by weight of higher functionality polyisocyanates of the diphenylmethane series,
      (2) 40 to 100% by weight of 4,4'-diphenylmethane diisocyanate,
      (3) 0 to 20% by weight of 2,4'-diphenylmethane diisocyanate, and
      (4) 0 to 6% by weight of 2,2'-diphenylmethane diisocyanate, with the sum of the %'s by weight of (B)(1), (B)(2), (B)(3) and (B)(4) totalling 100% by weight of (B);
   wherein the sum of the %'s by weight of (A) and (B) total 100% by weight; with
(II) an organic component containing from about 1.5 to about 4 hydroxyl groups, preferably 1.8 to 3 hydroxyl groups, and having a molecular weight of from about 76 to about 6,000, preferably of about 76 to about 4,800.

DETAILED DESCRIPTION OF THE INVENTION

In accordance with the present invention, the term "liquid" means that the partially trimerized product does not precipitate solids when stored at 25° C. for 3 months; and the term "storage-stable" means that the partially trimerized product has up to a 1% absolute change in the % NCO group content and up to a 10% change in the viscosity when stored at 25° C. for 3 months.

The liquid, partially trimerized polyisocyanates of the present invention comprise:
(A) from 20 to 88% by weight, preferably from 25 to 80%, and most preferably from 35 to 70%, of toluene diisocyanate; and
(B) from 12 to 80% by weight, preferably from 20 to 75%, and most preferably from 30 to 65%, of a polyisocyanate of the diphenylmethane series,
wherein the sum of the %'s by weight of (A) and (B) totals 100% by weight of the polyisocyanate composition.

These storage-stable, liquid partially trimerized polyisocyanates have an NCO group content of 24 to 40% by weight, preferably 26 to 38% by weight, and most preferably of 28 to 36% by weight. It is preferred that the trimer content of these storage-stable, liquid, partially trimerized polyisocyanate is at least 10%, more preferably at least 20% and most preferably at least 25% by weight.

Toluene diisocyanate (A) used in the present invention has an isomer distribution of (1) from 60 to 100% by weight, preferably 65 to 90%, and most preferably 65 to 80% of the 2,4-isomer; and (2) from 0 to 40% by weight, preferably 10 to 35%, and most preferably 20 to 35% of the 2,6-isomer;

wherein the sum of the %'s by weight of (A)(1) and (A)(2) totals 100% by weight of (A).

Suitable polyisocyanates of the diphenylmethane series to be used as (B) in the present invention comprises:

(1) from 0 to 50%, preferably 0 to 40%, and most preferably 0 to 30% by weight of higher functionality polyisocyanates of the diphenylmethane series;

(2) from 40 to 100%, preferably 45 to 100%, and most preferably 59 to 100% by weight of 4,4'-diphenylmethane diisocyanate;

(3) from 0 to 20%, preferably 1 to 15%, and most preferably 2 to 10% by weight of 2,4'-diphenylmethane diisocyanate; and (4) from 0 to 6%, preferably 0 to 3%, and most preferably 0 to 1% by weight of 2,2'-diphenylmethane diisocyanate;

wherein the sum of the %'s by weight of (B)(1), (B)(2), (B)(3) and (B)(4) totals 100% by weight of (B).

Suitable trimerization catalysts for the present invention include catalysts such as, for example, substituted guanidines such as, for example, tetramethyl guanidine, Mannich bases such as, for example, 2,4,6-bis(dimethylaminoethyl)phenol, and alkali metals salts of carboxylic acids. Any other catalysts known to be effective in trimerization reactions can also be used in the present invention. A preferred catalyst is methylene-bis(3,3',5,5'-tetra-dimethylaminomethyl-2,2'-phenol).

Suitable acidic stoppers for the present invention include compounds such as, for example, benzoyl chloride, anhydrous hydrochloric acid, sulfuric acid, bis(2-ethylhexyl) hydrogen phosphate, Lewis acids, etc. Preferred stoppers include benzoyl chloride and bis(2-ethylhexyl)hydrogen phosphate.

Suitable organic components which contain isocyanate-reactive hydroxyl groups include, for example, those compounds containing about 1.5 to about 4 hydroxyl groups, preferably about 1.8 to about 3 hydroxyl groups, and having a molecular weight of about 76 to about 6,000, preferably about 76 to about 4,800. Some examples of suitable compounds to be used as the organic component in forming the prepolymer are polyether polyols, polyester polyols, and diols.

Polyether polyols suitable for this aspect of the present invention include those having hydroxyl functionalities of from about 1.5 to about 4, preferably from about 1.8 to about 3, and molecular weights of from about 300 to about 6,000, preferably from about 800 to about 2,000, to yield a urethane prepolymer having an NCO content of from about 10 to about 38%, preferably about 20% to about 35%. Suitable polyester polyols to be used as the organic component containing isocyanate-reactive groups for this aspect of the present invention includes those compounds having hydroxyl functionalities of about 1.8 to about 2, and preferably about 2, and molecular weights of about 200 to about 3,000, preferably of about 500 to about 2,000 to yield a urethane prepolymer having an NCO group content of from about 10 to about 38%, preferably from about 20% to about 35%.

Suitable diols to be used as organic components which contain isocyanate-reactive groups in the formation of urethane prepolymers include compounds such as, for example, 1,3-butanediol, propylene glycol, 2,2,4-trimethyl-1,3-pentanediol, 2-methyl-1,3-propanediol, dipropylene glycol, tripropylene glycol, diethylene glycol and triethylene glycol. Preferred diols include 1,3-butanediol, propylene glycol, dipropylene glycol, and tripropylene glycol.

The process of the present invention comprises blending toluene diisocyanate and a specified polyisocyanate of the diphenylmethane series at 25 to 50° C., adding a trimerization catalyst to this mixture in an amount of about 0.01 to about 0.1% by weight, based on the entire weight of the isocyanate mixture, followed by heating the mixture at temperatures of from about 50 to about 200° C., preferably from about 80 to about 120° C., for a time period of from about 10 to about 500 minutes, preferably from about 20 to about 240 minutes. After the desired NCO group content of the reaction mixture is reached, a catalyst stopper is added in an amount such that there are about 2 equivalents of catalyst stopper for each mole of catalyst, to neutralize the catalyst remaining in the reaction mixture.

The process for the preparation of liquid urethane prepolymers having an NCO content of about 10 to about 38% from a liquid, partially trimerized polyisocyanate having an NCO content of about 24 to about 40% by weight comprises reacting the partially trimerized polyisocyanate with an isocyanate-reactive component containing from about 1.5 to about 4 hydroxyl groups and having a molecular weight of from about 76 to about 6,000, most preferably between about 76 and about 4,800, at temperatures between 40 and 120° C., preferably between 50 and 80° C. for a time of from 0.5 to 4 hours, preferably of from 1 to 3 hours.

The following examples further illustrate details for the preparation and use of the compositions of this invention. The invention, which is set forth in the foregoing disclosure, is not to be limited either in spirit or scope by these examples. Those skilled in the art will readily understand that known variations of the conditions and processes of the following preparative procedures can be used to prepare these compositions. Unless otherwise noted, all temperatures are degrees Celsius and all parts and percentages are parts by weight and percentages by weight, respectively.

EXAMPLES

The following materials were used in the working examples:

TDI: an isomeric mixture having an NCO content of about 48.27% and comprising 80% by weight of 2,4-toluene diisocyanate and 20% by weight of 2,6-toluene diisocyanate MDI-1: an isomeric mixture having an NCO content of about 33.6% and comprising about 98.4% by weight of 4,4'-diphenylmethane diisocyanate and about 1.6% by weight of 2,4'-diphenylmethane diisocyanate MDI-2: a polyisocyanate having an NCO content of about 31.5% and a functionality of about 2.7, and comprising about 44% by weight of diphenylmethane diisocyanate and about 56% by weight of higher homologues of diphenylmethane diisocyanate. The 44% by weight of diphenylmethane diisocyanate consists of about 41% by weight of the 4,4'-isomer of MDI and about 3% by weight of the 2,4'-isomer of MDI.

Catalyst A: methylene-bis(3,3',5,5'-tetra-dimethylaminomethyl-2,2'-phenol)

Example 1

To a 500 ml 3-neck flask, equipped with a stirrer, thermometer and a nitrogen pad, were added 101.4 parts by weight of MDI-1 and 188.3 parts by weight of TDI. To this mixture at 32° C., was added 0.06 part by weight of Catalyst A. The mixture was then heated to 90° C. and held at that temperature for 80 minutes, followed by the addition of 0.12 part by weight of benzoyl chloride and then cooled to 22° C.

The clear, colorless liquid had an NCO group content of 33.2% and a viscosity of 5560 mPa.s at 25° C. After storage at 22° C. for 22 weeks, the product remained a clear liquid.

Examples 2–17

The procedure of Example 1 was repeated at 90° C. using the reaction mixtures as listed in Table 1 below. The amount of benzoyl chloride used in each example was double the amount of Catalyst A used in each example. All the products listed in Table 1 were clear liquids and storage-stable at 22° C. for 22 weeks. The reaction time, percent (%) NCO of the partially trimerized isocyanate mixture and viscosity are also listed in Table 1.

TABLE 1

| Example | Reaction Mixture, pbw | | Reaction Time, min. | % NCO, Final | Visc. at 25° C., mPa.s |
|---|---|---|---|---|---|
| 1 | 101.4 | MDI-1 | 80 | 33.2 | 5,560 |
|   | 188.3 | TDI |  |  |  |
|   | 0.06 | Catalyst A |  |  |  |
| 2 | 70 | TDI | 60 | 31.8 | 32,100 |
|   | 30 | MDI-1 |  |  |  |
|   | 0.030 | Catalyst A |  |  |  |
| 3 | 60 | TDI | 90 | 32.3 | ,1000 |
|   | 40 | MDI-1 |  |  |  |
|   | 0.013 | Catalyst A |  |  |  |
| 4 | 55 | TDI | 80 | 30.8 | 952 |
|   | 45 | MDI-1 |  |  |  |
|   | 0.010 | Catalyst A |  |  |  |
| 5 | 50 | TDI | 50 | 33.6 | 286 |
|   | 50 | MDI-1 |  |  |  |
|   | 0.030 | Catalyst A |  |  |  |
| 6 | 45 | TDI | 80 | 32.0 | 462 |
|   | 55 | MDI-1 |  |  |  |
|   | 0.010 | Catalyst A |  |  |  |
| 7 | 40 | TDI | 70 | 33.3 | 92 |
|   | 60 | MDI-1 |  |  |  |
|   | 0.030 | Catalyst A |  |  |  |
| 8 | 60 | TDI | 180 | 36.1 | 52 |
|   | 40 | MDI-1 |  |  |  |
|   | 0.020 | Catalyst A |  |  |  |
| 9 | 34 | TDI | 45 | 24.3 | 126,600 |
|   | 66 | MDI-1 |  |  |  |
|   | 0.040 | Catalyst A |  |  |  |
| 10 | 28.5 | TDI | 140 | 28.4 | 36,900 |
|   | 71.5 | MDI-2 |  |  |  |
|   | 0.400 | Catalyst A |  |  |  |
| 11 | 35.7 | TDI | 160 | 30.2 | 710 |
|   | 28.6 | MDI-1 |  |  |  |
|   | 35.7 | MDI-2 |  |  |  |
|   | 0.180 | Catalyst A |  |  |  |
| 12 | 70 | TDI | 165 | 34.0 | 5,400 |
|   | 21 | MDI-1 |  |  |  |
|   | 9 | MDI-2 |  |  |  |
|   | 0.32 | Catalyst A |  |  |  |
| 13 | 80.0 | TDI |  |  |  |
|   | 2.1 | MDI-1 |  |  |  |
|   | 17.9 | MDI-2 | 130 | 39.7 | 15 |
|   | 0.23 | Catalyst A |  |  |  |
| 14 | 35 | TDI |  |  |  |
|   | 56 | MDI-1 |  |  |  |
|   | 9 | MDI-2 | 160 | 32.5 | 199 |
|   | 0.07 | Catalyst A |  |  |  |
| 15 | 35 | TDI |  |  |  |
|   | 56 | MDI-1 |  |  |  |
|   | 9 | MDI-2 | 200 | 28.7 | 68,800 |
|   | 0.10 | Catalyst A |  |  |  |
| 16 | 25.0 | TDI |  |  |  |
|   | 57.1 | MDI-1 |  |  |  |
|   | 17.9 | MDI-2 | 95 | 31.8 | 200 |
|   | 0.13 | Catalyst A |  |  |  |
| 17 | 25.0 | TDI |  |  |  |
|   | 57.1 | MDI-1 |  |  |  |
|   | 17.9 | MDI-2 | 140 | 32.2 | 215 |
|   | 0.17 | Catalyst A |  |  |  |

The following materials were used in the working examples demonstrating the stable, liquid prepolymers of the partial trimerization products above, and a process for their production.

TPG: Tripropylene glycol

PG: 1,2-propylyene glycol

XB: 1,3-butanediol

Polyol A: a propylene glycol/propylene oxide adduct having a molecular weight of about 425 and an OH number of about 265

Polyol B: a propylene glycol/propylene oxide adduct having a molecular weight of about 1,000 and an OH number of about 112

Example 18

To a 500 ml 3-neck flask equipped with a stirrer, thermometer and a nitrogen pad, were added 200 parts of the mixed trimer of Example 17. To the stirred isocyanate at 40° C. was added 21 parts of TPG. The resulting mixture was held at 65° C. for 2 hours, then cooled to 25° C. The clear liquid had an NCO group content of 24.9% and a viscosity of 19,000 mPa.s at 25° C.

Examples 19–29

The procedure of Example 18 was repeated, using the reaction mixtures as listed in Table 2 below. All the products listed in Table 2 were clear liquids and storage stable at 22° C. for 4 weeks, and then the tests were terminated.

TABLE 2

| Example | Reaction Mixture | PBW of Reaction Mixture | % NCO of Final Product | Viscosity at 25° C., mPa.s |
|---|---|---|---|---|
| 19 | Isocyanate of Ex. 17; Polyol A | 200; 32 | 25.0% | 4,960 |
| 20 | Isocyanate of Ex. 17; Polyol B | 200; 44 | 25.1% | 1,390 |
| 21 | Isocyanate of Ex. 14; TPG | 200; 21 | 25.0% | 12,560 |
| 22 | Isocyanate of Ex. 14; Polyol A | 200; 32 | 24.9% | 3,860 |
| 23 | Isocyanate of Ex. 14; Polyol B | 200; 44 | 24.9% | 1,260 |
| 24 | Isocyanate of Ex. 7; PG | 100; 3.1 | 29.0% | 1,240 |
| 25 | Isocyanate of Ex. 7; XB | 100; 4.4 | 27.9% | 2,270 |
| 26 | Isocyanate of Ex. 7; Polyol B | 100; 20 | 26.4% | 1,090 |
| 27 | Isocyanate of Ex. 8; PG | 100; 4.35 | 29.9% | 1,850 |
| 28 | Isocyanate of Ex. 8; XB | 100; 4.95 | 29.8% | 1,510 |
| 29 | Isocyanate of Ex. 8; Polyol B | 100; 19 | 29.0% | 650 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A storage-stable, liquid, partially trimerized polyisocyanate having an NCO group content of 24 to 40% by weight, and comprising the partial trimerization product of:
   (A) from 20 to 88% by weight of toluene diisocyanate having an isomer distribution of:
      (1) from 60 to 100% by weight of the 2,4-isomer, and
      (2) from 0 to 40% by weight of the 2,6-isomer, with the sum of the %'s by weight of (A)(1) and (A)(2) totalling 100% by weight of (A); and
   (B) from 12 to 80% by weight of a polyisocyanate of the diphenylmethane series comprising from:
      (1) 0 to 50% by weight of higher functionality polyisocyanates of the diphenylmethane series,
      (2) 40 to 100% by weight of 4,4'-diphenylmethane diisocyanate,
      (3) 0 to 20% by weight of 2,4'-diphenylmethane diisocyanate, and
      (4) 0 to 6% by weight of 2,2'-diphenylmethane diisocyanate,
      with the sum of the %'s by weight of (B)(1), (B)(2), (B)(3) and (B)(4) totalling 100% by weight of (B);
   wherein the sum of the %'s by weight of (A) and (B) total 100% by weight.

2. The storage-stable, liquid, partially trimerized polyisocyanate of claim 1, wherein the trimer content is at least 10% by weight, based on 100% by weight of the polyisocyanate.

3. The storage-stable, liquid, partially trimerized polyisocyanate of claim 1, wherein the trimer content is at least 20% by weight, based on 100% by weight of the polyisocyanate.

4. The storage-stable, liquid, partially trimerized polyisocyanate of claim 1, wherein the trimer content is at least 25% by weight, based on 100% by weight of the polyisocyanate.

5. A storage-stable, liquid, partially trimerized polyisocyanate having an NCO group content of 26 to 38% by weight, and comprising the partial trimerization product of:
   (A) from 25 to 80% by weight of toluene diisocyanate having an isomer distribution of:
      (1) from 65 to 90% by weight of the 2,4-isomer, and
      (2) from 10 to 35% by weight of the 2,6-isomer, wherein the sum of the %'s by weight of (A)(1) and (A)(2) totals 100% by weight of (A); and
   (B) from 20 to 75% by weight of a polyisocyanate of the diphenylmethane series comprising from:
      (1) 0 to 40% by weight of higher functionality polyisocyanates of the diphenylmethane series,
      (2) 45 to 100% by weight of 4,4'-diphenylmethane diisocyanate,
      (3) from 1 to 15% by weight of 2,4'-diphenylmethane diisocyanate, and
      (4) from 0 to 3% by weight of 2,2'-diphenylmethane diisocyanate,
      wherein the sum of the %'s by weight of (B)(1), (B)(2), (B)(3) and (B)(4) totals 100% by weight of (B);
   wherein the sum of the %'s by weight of (A) and (B) total 100% by weight.

6. A process for the preparation of a storage-stable, liquid, partially trimerized polyisocyanate composition containing isocyanurate groups and having an NCO group content of about 24 to about 40% by weight, comprising:
   (1) partially trimerizing:
      (A) from 20 to 88% by weight of toluene diisocyanate having an isomer distribution of:
         (1) from 60 to 100% by weight of the 2,4-isomer, and
         (2) from 0 to 40% by weight of the 2,6-isomer, with the sum of the %'s by weight of (A)(1) and (A)(2) totalling 100% by weight of (A); and
      (B) from 12 to 80% by weight of a polyisocyanate of the diphenylmethane series comprising from:
         (1) 0 to 50% by weight of higher functionality polyisocyanates of the diphenylmethane series,
         (2) 40 to 100% by weight of 4,4'-diphenylmethane diisocyanate,
         (3) 0 to 20% by weight of 2,4'-diphenylmethane diisocyanate, and
         (4) 0 to 6% by weight of 2,2'-diphenylmethane diisocyanate,
         with the sum of the %'s by weight of (B)(1), (B)(2), (B)(3) and (B)(4) totalling 100% by weight of (B);
      wherein the sum of the %'s by weight of (A) and (B) total 100% by weight, in the presence of:
   (C) at least one trimerization catalyst, followed by the addition of:
   (D) an acidic stopper.

7. The process of claim 6, wherein the trimer content of the storage-stable, liquid, partially trimerized polyisocyanate composition is at least 10% by weight, based on 100% by weight of the polyisocyanate.

8. The process of claim 7, wherein the trimer content is at least 20% by weight, based on 100% by weight of the polyisocyanate.

9. The process of claim 7, wherein the trimer content is at least 25% by weight, based on 100% by weight of the polyisocyanate.

10. The process of claim 6, wherein the storage-stable, liquid, partially trimerized polyisocyanate composition has an NCO group content of about 26 to about 38% by weight, and comprises:
    (A) from 25 to 80% by weight of toluene diisocyanate having an isomer distribution of:
       (1) from 65 to 90% by weight of the 2,4-isomer, and
       (2) from 10 to 35% by weight of the 2,6-isomer, wherein the sum of the %'s by weight of (A)(1) and (A)(2) totals 100% by weight of (A); and
    (B) from 20 to 75% by weight of a polyisocyanate of the diphenylmethane series comprising from:
       (1) 0 to 40% by weight of higher functionality polyisocyanates of the diphenylmethane series,
       (2) 45 to 100% by weight of 4,4'-diphenylmethane diisocyanate,
       (3) from 1 to 15% by weight of 2,4'-diphenylmethane diisocyanate, and
       (4) from 0 to 3% by weight of 2,2'-diphenylmethane diisocyanate,
       wherein the sum of the %'s by weight of (B)(1), (B)(2), (B)(3) and (B)(4) totals 100% by weight of (B);
    wherein the sum of the %'s by weight of (A) and (B) total 100% by weight.

11. A storage-stable, liquid prepolymer containing a mixed trimer of toluene diisocyanate and a polyisocyanate of the diphenylmethane series, having an NCO group content of about 10 to about 38% by weight, and comprising the reaction product of:
    (I) the liquid, partially trimerized polyisocyanate of claim 1, and
    (II) an organic component containing from about 1.5 to about 4 hydroxyl groups which are capable of reacting with NCO groups, and having a molecular weight of from about 76 to about 6,000.

12. The storage-stable, liquid prepolymer of claim 11, wherein (II) said organic component contains from about 1.8 to 3 hydroxyl groups and has an molecular weight of about 76 to about 4,800.

13. The storage-stable, liquid prepolymer of claim 11, wherein (II) said organic component comprises a polyether polyol having an equivalent weight of at least about 900 and containing at least about 10% by weight of ethylene oxide, based on 100% by weight of alkylene oxide.

14. The storage-stable, liquid prepolymer of claim 11, wherein the NCO group content is from about 20 to about 35% by weight.

15. The storage-stable, liquid prepolymer of claim 11, wherein (I) the liquid, partially trimerized polyisocyanate contains at least about 10% by weight of trimer.

16. The storage-stable, liquid prepolymer of claim 11, wherein (I) the liquid, partially trimerized polyisocyanate has an NCO group content of 26 to 38% by weight.

17. A process for the production of a storage-stable, liquid prepolymer having an NCO group content of about 10 to about 38% by weight, containing a mixed trimer of toluene diisocyanate and a polyisocyanate of the diphenylmethane series, comprising:
  (1) reacting
    (I) the liquid, partially trimerized polyisocyanate produced by the process of claim 5, with
    (II) an organic component containing from about 1.5 to about 4 hydroxyl groups which are capable of reacting with NCO groups and having a molecular weight of from about 76 to about 6,000.

18. The process of claim 17, wherein (II) said organic component contains from about 1.8 to about 3 hydroxyl groups and has a molecular weight of about 76 to about 4,800.

19. The process of claim 17, wherein (II) said organic component comprises a polyether polyol having an equivalent weight of at least about 900 and containing at least about 10% by weight of ethylene oxide, based on 100% by weight of alkylene oxide.

20. The process of claim 17, wherein the NCO group content is from about 20 to about 35% by weight.

21. The process of claim 17, wherein (I) the liquid, partially trimerized polyisocyanate contains at least about 10% by weight of trimer.

22. The process of claim 17, wherein (I) the liquid, partially trimerized polyisocyanate has an NCO group content of 26 to 38% by weight.

* * * * *